US012590298B2

(12) United States Patent
Sun et al.

(10) Patent No.: US 12,590,298 B2
(45) Date of Patent: Mar. 31, 2026

(54) EX VIVO TUMOR ANGIOGENESIS MODEL

(71) Applicant: THE REGENTS OF THE UNIVERSITY OF CALIFORNIA, Oakland, CA (US)

(72) Inventors: Hui Sun, Los Angeles, CA (US); Adrian Chichuen Au, Los Angeles, CA (US); Guo Cheng, Los Angeles, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 920 days.

(21) Appl. No.: 17/769,182

(22) PCT Filed: Oct. 16, 2020

(86) PCT No.: PCT/US2020/056020
§ 371 (c)(1),
(2) Date: Apr. 14, 2022

(87) PCT Pub. No.: WO2021/076915
PCT Pub. Date: Apr. 22, 2021

(65) Prior Publication Data
US 2024/0101965 A1      Mar. 28, 2024

Related U.S. Application Data

(60) Provisional application No. 62/916,997, filed on Oct. 18, 2019.

(51) Int. Cl.
| | |
|---|---|
| *C12N 5/09* | (2010.01) |
| *C12N 5/071* | (2010.01) |
| *G01N 33/50* | (2006.01) |

(52) U.S. Cl.
CPC ........... *C12N 5/0693* (2013.01); *C12N 5/069* (2013.01); *G01N 33/5011* (2013.01); *C12N 2503/02* (2013.01)

(58) Field of Classification Search
CPC . C12N 5/0693; C12N 2503/02; C12N 5/0062
See application file for complete search history.

(56) References Cited

U.S. PATENT DOCUMENTS

| | | | |
|---|---|---|---|
| 5,342,444 | A | 8/1994 | Harnisch et al. |
| 5,374,514 | A | 12/1994 | Kirk et al. |
| 5,380,713 | A | 1/1995 | Balasubramanian et al. |
| 5,565,408 | A | 10/1996 | Hagen et al. |
| 5,576,338 | A | 11/1996 | Friesen et al. |
| 5,624,937 | A | 4/1997 | Reel et al. |
| 5,939,248 | A | 8/1999 | Kirk et al. |
| 6,258,822 | B1 | 7/2001 | Geyer et al. |
| 6,262,074 | B1 | 7/2001 | Otten et al. |
| 6,284,796 | B1 | 9/2001 | Geyer et al. |
| 6,479,436 | B1 | 11/2002 | Otten et al. |
| 6,504,031 | B1 | 1/2003 | Bruncko et al. |
| 6,576,644 | B2 | 6/2003 | Bi et al. |
| 6,583,156 | B1 | 6/2003 | Gillespie et al. |
| 6,602,882 | B1 | 8/2003 | Davies et al. |
| 6,639,121 | B1 | 10/2003 | DePinho et al. |
| 6,803,369 | B1 | 10/2004 | Erskine et al. |
| 6,927,214 | B1 | 8/2005 | Teng et al. |
| 6,962,917 | B2 | 11/2005 | Davies et al. |
| 7,141,564 | B2 | 11/2006 | Brooks et al. |
| 7,186,730 | B2 | 3/2007 | Dartois et al. |
| 7,205,408 | B2 | 4/2007 | Davies et al. |
| 7,232,832 | B2 | 6/2007 | Axten et al. |
| 7,511,157 | B2 | 3/2009 | Bailey et al. |
| 7,576,215 | B2 | 8/2009 | Collini et al. |
| 7,592,334 | B2 | 9/2009 | Miller et al. |
| 7,605,169 | B2 | 10/2009 | Miller et al. |
| 7,648,984 | B2 | 1/2010 | Miller et al. |
| 7,692,017 | B2 | 4/2010 | Dinsmore et al. |
| 7,705,043 | B2 | 4/2010 | Alonso-Alija et al. |
| 7,732,613 | B2 | 6/2010 | Kim |
| 7,776,910 | B2 | 8/2010 | Lopez-Tapia et al. |
| 7,928,111 | B2 | 4/2011 | Tachdjian et al. |
| 7,973,164 | B2 | 7/2011 | Jung et al. |
| 7,977,354 | B2 | 7/2011 | Marsais et al. |
| 8,008,306 | B2 | 8/2011 | Koura et al. |
| 8,063,220 | B2 | 11/2011 | Galambos et al. |
| 8,222,297 | B2 | 7/2012 | Su et al. |
| 8,278,342 | B2 | 10/2012 | Ricciardi |

(Continued)

FOREIGN PATENT DOCUMENTS

| | | |
|---|---|---|
| CN | 102516232 | 6/2012 |
| DE | 102008010661 | 9/2009 |

(Continued)

OTHER PUBLICATIONS

Bayin. 2016, Neoplasia, 18:12, 795-805.*
Jiang, et al. "A novel peptide isolated from a phage display peptide library with trastuzumab can mimic antigen epitope of HER-2", *J. Biol. Chem,* 280, pp. 4656-5662, 2005.
Office Action issued in corresponding U.S. Appl. No. 17/072,952, dated Dec. 16, 2022.
Stancovski, et al. "Mechanistic aspects of the opposing effects of monoclonal antibodies to the ERBB2 receptor on tumor growth", *Proc. Natl. Acad. Sci.,* vol. 88, pp. 8691-8695, 1991.

(Continued)

*Primary Examiner* — Valarie E Bertoglio

(74) *Attorney, Agent, or Firm* — Norton Rose Fulbright US LLP

(57) ABSTRACT

The present disclosure relates generally to ex vivo primary tumor models prepared from fresh tumor tissues which are useful for screening anti-cancer agents. The fresh tumor tissues are prepared and cultured under suitable conditions to grow an outgrowth of endothelial cells. Killing of these endothelial cells by a candidate agent indicates the efficacy of the agent in inhibiting tumor angiogenesis.

14 Claims, 4 Drawing Sheets

(56)                    References Cited

U.S. PATENT DOCUMENTS

| | | | |
|---|---|---|---|
| 8,623,877 | B2 | 1/2014 | Gao et al. |
| 8,642,660 | B2 | 2/2014 | Goldfarb |
| 8,772,200 | B2 | 7/2014 | Shibayama et al. |
| 8,829,002 | B2 | 9/2014 | Ivachtchenko et al. |
| 8,975,259 | B2 | 3/2015 | Smrcka et al. |
| 9,000,054 | B2 | 4/2015 | Tachdjian et al. |
| 9,127,000 | B2 | 9/2015 | Ren et al. |
| 9,573,950 | B2 | 2/2017 | Backfisch et al. |
| 9,586,964 | B2 | 3/2017 | Lindsley et al. |
| 9,595,683 | B2 | 3/2017 | Choi et al. |
| 9,688,635 | B2 | 6/2017 | Qian et al. |
| 10,093,628 | B2 | 10/2018 | Knape et al. |
| 10,227,350 | B2 | 3/2019 | Chandrasekhar et al. |
| 10,244,779 | B2 | 4/2019 | Tachdjian et al. |
| 11,884,647 | B2 | 1/2024 | Sun et al. |
| 2002/0177121 | A1* | 11/2002 | Woltering et al. ..... A61K 45/00 |
| 2003/0212084 | A1 | 11/2003 | Hatton et al. |
| 2004/0053928 | A1 | 3/2004 | Davies et al. |
| 2004/0077655 | A1 | 4/2004 | Dartois et al. |
| 2004/0077656 | A1 | 4/2004 | Markwell et al. |
| 2004/0198756 | A1 | 10/2004 | Davies et al. |
| 2005/0261298 | A1 | 11/2005 | Solow-Cordero et al. |
| 2006/0040925 | A1 | 2/2006 | Davies et al. |
| 2006/0111368 | A1 | 5/2006 | Osakada et al. |
| 2006/0189601 | A1 | 8/2006 | Hennessy et al. |
| 2007/0254872 | A1 | 11/2007 | Miller et al. |
| 2008/0194547 | A1 | 8/2008 | Miller et al. |
| 2009/0036485 | A1 | 2/2009 | Jung |
| 2009/0042910 | A1 | 2/2009 | Jung et al. |
| 2009/0076075 | A1 | 3/2009 | Jung et al. |
| 2009/0270371 | A1 | 10/2009 | Keseru et al. |
| 2009/0275611 | A1 | 11/2009 | Riether et al. |
| 2010/0113513 | A1 | 5/2010 | Murphy Kessabi et al. |
| 2010/0255528 | A1 | 10/2010 | Zudaire et al. |
| 2011/0065891 | A1 | 3/2011 | Fang et al. |
| 2011/0230476 | A1 | 9/2011 | Niu et al. |
| 2011/0275643 | A1 | 11/2011 | Liou et al. |
| 2012/0071505 | A1 | 3/2012 | Gaddam et al. |
| 2013/0079342 | A1 | 3/2013 | Dransfield et al. |
| 2013/0090323 | A1 | 4/2013 | Dransfield et al. |
| 2013/0274215 | A1 | 10/2013 | Thies et al. |
| 2013/0344165 | A1 | 12/2013 | Boden et al. |
| 2014/0182680 | A1 | 7/2014 | Kawata et al. |
| 2015/0259326 | A1 | 9/2015 | Kesari et al. |
| 2016/0155575 | A1 | 6/2016 | Yamato et al. |
| 2017/0007610 | A1 | 1/2017 | Desai et al. |
| 2017/0174653 | A1 | 6/2017 | Sherer et al. |
| 2017/0260278 | A1 | 9/2017 | Youngro et al. |
| 2017/0281611 | A1 | 10/2017 | Dahl |
| 2018/0086719 | A1 | 3/2018 | Chandrasekhar et al. |
| 2018/0179199 | A1 | 6/2018 | Dreas et al. |
| 2018/0244995 | A1 | 8/2018 | Xia et al. |
| 2019/0010136 | A1 | 1/2019 | Danjo et al. |
| 2021/0147385 | A1 | 5/2021 | Sun et al. |
| 2021/0147525 | A1 | 5/2021 | Sun et al. |

FOREIGN PATENT DOCUMENTS

| | | | |
|---|---|---|---|
| EP | 2401915 | | 1/2012 |
| EP | 2402338 | | 1/2012 |
| GB | 2208862 | | 4/1989 |
| JP | 02262627 | | 10/1990 |
| JP | 05039272 | | 2/1993 |
| JP | 08157461 | | 6/1996 |
| JP | 2005126549 | | 5/2005 |
| JP | 2009-520014 | | 5/2009 |
| JP | 2016153479 | | 8/2016 |
| JP | 2016162983 | | 9/2016 |
| KR | 2011 0136147 | A | 12/2011 |
| KR | 101 748 707 | B1 | 6/2017 |
| WO | 95/11592 | | 5/1995 |
| WO | 95/023968 | | 9/1995 |
| WO | 98/05652 | | 2/1998 |
| WO | 98/12192 | | 3/1998 |
| WO | 99/05096 | | 2/1999 |
| WO | 2002/042267 | | 5/2002 |
| WO | 2006/008644 | | 1/2006 |
| WO | 2007/072093 | | 6/2007 |
| WO | 2007/138112 | | 12/2007 |
| WO | 2008/010061 | | 1/2008 |
| WO | 2008/049047 | | 4/2008 |
| WO | 2008/066691 | | 6/2008 |
| WO | 2009/019708 | | 2/2009 |
| WO | 2009/153589 | | 12/2009 |
| WO | 2011/143348 | | 11/2011 |
| WO | 2011/156557 | | 12/2011 |
| WO | 2013/020909 | | 2/2013 |
| WO | 2013/158928 | | 10/2013 |
| WO | 2017/020030 | | 2/2017 |
| WO | 2017/072283 | | 5/2017 |
| WO | 2017/189715 | | 11/2017 |
| WO | 2018/035138 | | 2/2018 |
| WO | 2018/068357 | | 4/2018 |
| WO | 2018/130184 | | 7/2018 |
| WO | 2018/200498 | | 11/2018 |
| WO | 2018/202712 | | 11/2018 |
| WO | 2019/037678 | | 2/2019 |
| WO | 2019/174382 | | 9/2019 |
| WO | 2021/076886 | | 4/2021 |
| WO | 2021/076903 | | 4/2021 |
| WO | 2021/076915 | | 4/2021 |
| WO | WO 2023/204799 | | 10/2023 |

OTHER PUBLICATIONS

Au, Adrian, "Activation Mechanism and Novel Therapeutic Agent of a Membrane Receptor Involved in Pathogenic Angiogenesis", *ProQuest Dissertations Publishing*, 2020.

Bagley et al., "Tumor endothelial marker 7 (TEM-7): a novel target for antiangiogenic therapy", *Microvasc Res.*, 82(3):25-262, 2011.

Beaty et al., "PLXDC1 (TEM7) is identified in a genome-wide expression screen of glioblastoma endothelium." *J Neurooncol.*, 81(3):241-248, 2007.

Cheng et al., "Identification of PLXDC1 and PLXDC2 as the transmembrane receptors for the multifunctional factor PEDF", *eLife*,3:e05401, 2014.

Forest et al., "Optimization of immunostaining on flat-mounted human corneas." *Mol Vis.*, 21:1345-1356, 2015.

Galambos et al., "4-Aryl-3-arylsulfonyl-quinolines as negative allosteric modulators of metabotropic GluR5 receptors: From HTS hit to development candidate", *Bioorg Med Chem Lett.*, 26(4): 1249-1252, 2016.

Galambos et al., "Discovery and Preclinical Characterization of 3-((4-(4-Chlorophenyl)-7-fluoroquinoline-3-yl)sulfonyl)benzonitrile, a Novel Non-acetylenic Metabotropic Glutamate Receptor 5 (mGluR5) Negative Allosteric Modulator for Psychiatric Indications", *Journal of Medicinal Chemistry*, 60:2470-2484, 2017.

Galambos et al., "Discovery of 4-amino-3-arylsulfoquinolines, a novel non-acetylenic chemotype of metabotropic glutamate 5(mGlu$_5$) receptor negative allosteric modulators", *European Journal of Medicinal Chemistry*, 113(17):240-254, 2017.

Howat et al., "Tissue fixation and the effect of molecular fixatives on downstream staining procedures." *Methods.*, 70(1):12-19, 2014.

International Search Report and Written Opinion issued in International Application No. PCT/US2020/055979, mailed Dec. 22, 2020.

International Search Report and Written Opinion issued in International Application No. PCT/US2020/056003, mailed Feb. 17, 2021.

International Search Report and Written Opinion issued in International Application No. PCT/US2020/056020, mailed Feb. 4, 2021.

International Search Report and Written Opinion issued in International Application No. PCT/US2020/056039, mailed Mar. 26, 2021.

Ivachtchenko et al., "5-HT6 Receptor antagonists. I. Screening of the library of various heterocyclic compounds containing an alkysulfonyl moiety", *Pharmaceutical Chemistry Journal*, 46(1): 274-284, 2012.

Ivachtchenko et al., "Antagonists of Serotonin 5-HT6 Receptors. VI. Substituted 3-(Phenylsulfonyl)Quinolines, Synthesis and Structure-Activity Relationships", *Pharmaceutical Chemistry Journal*, 48(10): 646-660, 2015.

(56) References Cited

OTHER PUBLICATIONS

Kang et al., "One-pot Synthesis of Highly Functionalizable 3(Phenylsulfonyl)-2,3-dihydro-4(1H)quinolinones via a Cu-catalyzed Aza-Michael Addition/Cyclization Reaction", *Chem. Lett.*, 45:1356-1358, 2016.

Lee et al., "Identification of the basement membrane protein nidogen as a candidate ligand for tumor endothelial marker 7 in vitro and in vivo." *FEBS Lett.*, 580(9):2253-2257, 2006.

Li et al., "Cooper-Catalyzed Electrophilic Cyclization of N-Propargylamines with Sodium Sulfinate for the synthesis of 3-Sulfonated Quinolines", *Chem Asian J.*, 14(23):4358-4364, 2019.

Nowak-Sliwinska et al., "Consensus guidelines for the use and interpretation of angiogenesis assays", *Angiogenesis*, 21(3):425-532, 2018.

Shao et al., "Choroid sprouting assay: an ex vivo model of microvascular angiogenesis", *PLoS One.*, 8(7):369552, 2013.

Smusz et al., "Fingerprint-based consensus virtual screening towards structurally new 5-HT(6)R ligands", *Bioorg Med Chem Lett.*, 25(9):1827-1830, 2015.

Sun et al., "Visible-light-induced multicomponent cascase cycloaddition involving N-Propargyl aromatic amines, diaryliodonium salts and sulfur dioxide: rapid access to 3-arylsulfonylquinolines", *Chemical Communications*54(11):1335-1338, 2018.

Yamaji et al., "TEM7 (PLXDC1) in neovascular endothelial cells of fibrovascular membranes from patients with proliferation diabetic retinopathy", *Invest Ophthalmol Vis Sci.*, 49(7):3151-3157, 2008.

Yang et al., "An iron delivery pathway mediated by a lipocalin." *Mol Cell.*, 10(5):1045-1056, 2002.

Yang et al., "Discovery of Orally Bioavailable Quinoline-Based Aldehyde Dehydrogenase 1A1 (ALDH1A1) Inhibitors with Potent Cellular Activity", *Journal of Medicinal Chemistry*, 61:4883-4903, 2018.

Zhang et al., "Antiproliferative activities of the second-generation antipsychotic drug sertindole against breast cancers with a potential application for treatment of breast-to-brain metastases", *Sci Rep.*, 8(1):15753, 2018.

Zhang et al., "tert-Butyl Hydroperoxide Mediated Cascade Synthesis of 3-Arylsulfonylquinolines", *Org Lett.*, 18(6):1286-1289, 2016.

Balzano et al., "Nidogen-1 Contributes to the Interaction Network Involved in Pro-B Cell Retention in the Perisinusoidal Hematopoietic Stem Cell Niche", *Cell Reports*, 26:3257-3271, 2019.

CAS Registry No. 1351848-54-8 (Entered STN: Dec. 23, 2011).

Mayes et al. "The promise and challenges of immune agonist antibody development in cancer", *Nature Reviews Drug Discovery*, 17(7):509-527, 2018.

Zhang, Y. et al., "A visible-light-induced oxidative cyclization of N-propargylanilines with sulfinic acids to 3-sulfonated quinoline derivatives without external photocatalysts", *Chem. Commun.*, 55:2785-2788, 2019.

* cited by examiner

EX VIVO TUMOR ANGIOGENESIS MODEL

CROSS REFERENCE TO RELATED APPLICATIONS

This application is a national phase application under 35 U.S.C. § 371 of International Application No. PCT/US2020/056020 filed Oct. 16, 2020, which claims the benefit under 35 U.S.C. § 119 (e) of U.S. Provisional Ser. No. 62/916,997 filed Oct. 18, 2019, the content of which are incorporated by reference in their entirety into the present disclosure.

BACKGROUND

Costs of new anti-cancer drugs have increased constantly over the last decades, partly due to the increased difficulty in drug development. When considering all indications in oncology, less than ten percent of drug candidates that enter clinical development will reach regulatory approval. While there are several factors that contribute to the low success rate from bench to clinic, one significant challenge remains in the translatability of pre-clinical cancer models to the patient.

In vitro methods, such as scratch assays, transwell migration assays, and invasion assays only evaluate the ability of cells to migrate on or through a solid substratum, and do not recapitulate the anchorage-independence required for metastatic dissemination through the circulation. Furthermore, invasion assays fail to account for the differences in the extracellular matrix composition of primary and secondary sites. These shortcomings largely limit the use of standard in vitro methods to studies of either dissemination of tumor cells from the primary site or invasion of the secondary organ, but not both.

Conventional xenograft models offer the advantage of working with human cancer cells in vivo. A disadvantage, however, is that these human cells have been maintained in culture as cell lines, which can lead to significant differences between the properties and behavior of xenografted cells as compared to primary tumor cells. Another major disadvantage is that tumor blood vessels in mouse xenograft models are still mouse blood vessels, even for human tumor xenografts. In human tumor xenograft models, the tumor endothelial cells that support tumor growth are still mouse endothelial cells. To address the need to work with primary tumor cells, in vivo models that provide spontaneous tumors in mice have been developed (see, e.g., U.S. Pat. No. 6,639,121). In these models, however, the tumor cells are mouse tumor cells. This disclosure describes the development of 3-D models of human or animal tumor endothelial cells.

SUMMARY

The present disclosure, in various embodiments, describes ex vivo primary tumor angiogenesis assays developed to study the effects of therapeutic agents on tumor angiogenesis. The assays utilize an ex vivo primary tumor model generated from a tumor block dissected from a primary tumor tissue. The dissected tumor block, which may conform to preferred dimensions suitable for ex vivo growth, is embedded in a biological matrix, e.g., within hours, days, or weeks after removal from the organism, and cultured under conditions that promote growth of endothelial cells from the tumor block. Endothelial cells grow out of the tumor block and form a 2-dimensional or 3-dimensional outgrowth surrounding the tumor block, providing a suitable model system for drug testing. When treated with a candidate cancer therapeutic agent, death of the endothelial cells can effectively indicate the potential therapeutic efficacy of the agent on the tumor endothelial cells. In the same assay, the death of the tumor cells can be evaluated simultaneously to assess whether the reagent is specific to tumor endothelial cells or more generally cytotoxic.

In accordance with some embodiments of the present disclosure, therefore, provided is a method for growing endothelial cells around a tumor tissue, comprising embedding a tumor tissue, e.g., having a diameter between 0.1 mm and 1.5 mm, in a biological matrix; and culturing the tumor tissue in the biological matrix under conditions to promote growth of endothelial cells from the tumor tissue, for a time sufficient to allow the tumor tissue to grow, e.g., to larger than 2 mm in diameter. Also provided, in other embodiments, are tumor models capable of angiogenesis, prepared by the method of the present technology.

In some embodiments, the present disclosure provides a tumor endothelial tissue model prepared ex vivo, comprising at least one endothelial cell outgrowth surrounding a tumor core, e.g., wherein the tumor endothelial tissue model has a diameter between 0.5 mm and 20 mm; and the tumor core has a diameter that is greater than 0.2 mm but is not greater than 50% of the diameter of the tumor endothelial tissue model. Preferably, at least 50% of cells in the endothelial cell outgrowth are endothelial cells, e.g., grown, ex vivo, from the tumor core.

Methods of using the tumor endothelial tissue models to determine the efficacy of a candidate agent in killing tumor endothelial cells are also provided, which are useful for drug screening. In some embodiments, the method comprises contacting a tumor endothelial tissue model of the present disclosure with a candidate agent ex vivo; and assessing effects of the candidate agent on the endothelial cells surrounding the tumor core, e.g., by assessing proliferation of the endothelial cells, assessing growth of the endothelial cell outgrowth, determining the ratio of live to dead cells in the endothelial cells of the tumor endothelial tissue model, detecting cell death in the endothelial cells surrounding the tumor core (e.g., by detecting markers of apoptosis, necrosis, and/or cell lysis), or detecting a decrease in the thickness of the endothelial cell outgrowth of the tissue model, e.g., wherein detecting inhibition of growth and/or proliferation of endothelial cells, death of endothelial cells, a decrease in the thickness of the endothelial cell outgrowth, or a decreased ratio of live to dead cells in the endothelial cells compared to prior to the contact indicates that the candidate agent is capable of inhibiting proliferation of and/or killing tumor endothelial cells. In certain embodiments, the specificity of killing tumor endothelial cells can be assessed in the same model by evaluating the death of tumor cells in the model. If the candidate agent selectively kills tumor endothelial cells, relative to tumor cells in the tumor core, the candidate agent specifically targets tumor angiogenesis in vivo, and is not more generally cytotoxic (e.g., cytotoxic to multiple cell types, possibly including healthy cell types). In contrast, a nonspecific agent would kill both tumor endothelial cells and tumor cells.

BRIEF DESCRIPTION OF THE DRAWINGS

FIG. 1A presents a top view of the culture from the initial tumor embedding to the time of the start of the treatment when the tumor endothelial cells have grown out of the tumor. FIG. 1B presents a side view of the culture from the initial tumor embedding to the time of the start of the treatment when the tumor endothelial cell outgrowth may be smaller than that of the tumor core. FIG. 1C presents a side view of the culture from the initial tumor embedding to the time of the start of the treatment when the tumor endothelial cell outgrowth may be the same as or even greater than that of the tumor core.

FIG. 2A shows that the tumor endothelial cells treated with a negative control are alive (light gray) while the tumor core is a mixture (shading). FIG. 2B shows that an agent that has no effect on tumor endothelial cell death would be similar to the control treatment. FIG. 2C shows that an agent that indiscriminately kills all cells and has nonspecific toxicity would kill both the tumor and tumor endothelial cells. FIG. 2D shows that an agent that only kills tumor endothelial cells without affecting the tumor core is a highly specific agent for tumor endothelial cells.

FIG. 3A shows that all tumor endothelial cells and most of the tumor were alive (green) when treated with a control vehicle and that the middle of the tumor contained dead cells (orange). FIG. 3B shows that some tumor endothelial cells were killed (red) while the tumor was similar to the control when treated with 20 μM LCI-11 FIG. 3C shows that most of the tumor endothelial cells were killed (red) while the tumor was similar to the control when treated with 20 μM LCI38-W43 FIG. 3D shows that all tumor endothelial cells and all tumor cells were killed (red) when treated with 20 μM LCI38-W50.

FIG. 4A shows that all tumor endothelial cells and most of the tumor were alive (green) when treated with a control vehicle and that the middle of the tumor contained dead cells (orange). FIG. 4B shows that some tumor endothelial cells were killed (red) while the tumor was similar to the control when treated with 20 μM Comp A. FIG. 4C. shows that all of the tumor endothelial cells were killed (red) while the tumor was still alive (green) when treated with 20 μM Comp B. FIG. 4D shows that all tumor endothelial cells and all tumor cells were killed (red) when treated with 20 μM Comp C.

Figures 1A, 1B, 1C:
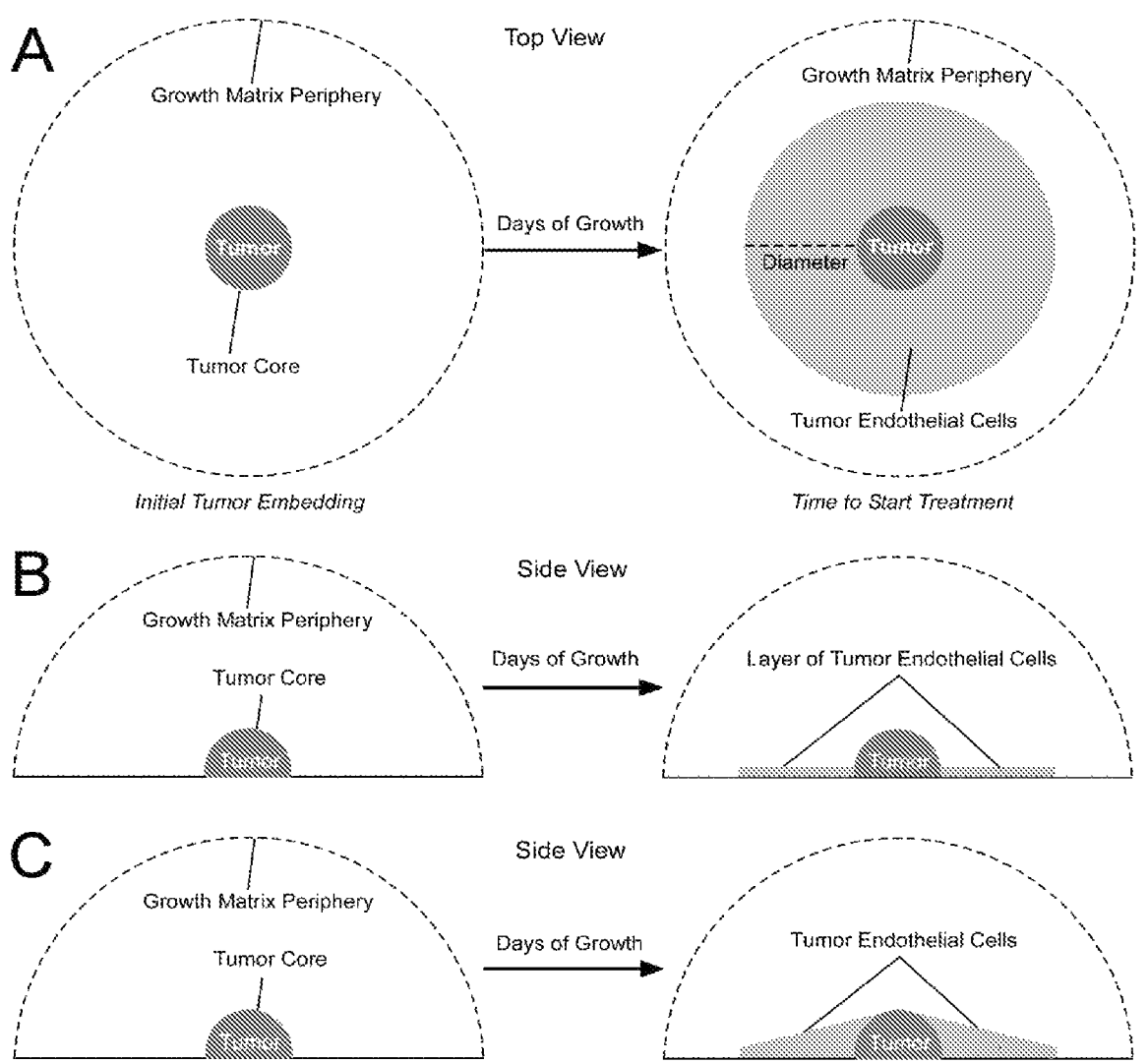
FIGS. 1A-1C show exemplary schematic diagrams of the ex vivo tumor endothelial cell model.

It will be recognized that some or all of the figures are schematic representations for purpose of illustration.

DETAILED DESCRIPTION

Definitions

For convenience, certain terms employed in the specification, examples, and appended claims are collected here.

The term "a small molecule" is a compound having a molecular weight of less than 2000 Daltons, preferably less than 1000 Daltons. Typically, a small molecule therapeutic is an organic compound that may help regulate a biological process.

The terms "decrease", "reduced", "reduction", or "inhibit" are all used herein to mean a decrease by a measurable amount. In some embodiments, "reduce," "reduction" or "decrease" or "inhibit" means a decrease by at least 10% as compared to a reference level (e.g., the absence of a given treatment) and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more.

The terms "increased", "increase" or "enhance" or "activate" are all used herein to generally mean an increase by a measurable amount. In some embodiments, the term "increased", "increase" or "enhance" or "activate" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, at least about a 20-fold increase, at least about a 50-fold increase, at least about a 100-fold increase, at least about a 1000-fold increase or more as compared to a reference level.

As used herein, the term "test compound" or "candidate agent" refers to an agent or collection of agents (e.g., compounds) that are to be screened for their ability to have an effect on the cell. Test compounds can include a wide variety of different compounds, including chemical compounds, mixtures of chemical compounds, e.g., polysaccharides, small organic or inorganic molecules (e.g., molecules having a molecular weight less than 2000 Daltons, less than 1000 Daltons, less than 1500 Daltons, less than 1000 Daltons, or less than 500 Daltons), biological macromolecules, e.g., peptides, proteins, peptide analogs, and analogs and derivatives thereof, peptidomimetics, nucleic acids, nucleic acid analogs and derivatives, an extract made from biological materials such as bacteria, plants, fungi, or animal cells or tissues, naturally occurring or synthetic compositions.

Depending upon the particular embodiment being practiced, the test compounds can be provided free in solution, or can be attached to a carrier, or a solid support, e.g., beads. A number of suitable solid supports can be employed for immobilization of the test compounds. Examples of suitable solid supports include agarose, cellulose, dextran (commercially available as, i.e., Sephadex, Sepharose) carboxymethyl cellulose, polystyrene, polyethylene glycol (PEG), filter paper, nitrocellulose, ion exchange resins, plastic films, polyaminemethylvinylether maleic acid copolymer, glass beads, amino acid copolymer, ethylene-maleic acid copolymer, nylon, silk, etc. Additionally, for the methods described herein, test compounds can be screened individually, or in groups. Group screening is particularly useful where hit rates for effective test compounds are expected to be low such that one would not expect more than one positive result for a given group.

Without limitation, the compounds can be tested at any concentration that can exert an effect on the cells relative to a control over an appropriate time period. In some embodiments, compounds are tested at concentrations in the range of about 0.01 nM to about 100 mM, about 0.1 nM to about 500 uM, about 0.1 μM to about 20 μM, about 0.1 μM to about 10 μM, or about 0.1 μM to about 5 μM.

The compound screening assay can be used in a high through-put screen. High through-put screening is a process in which libraries of compounds are tested for a given activity. High through-put screening seeks to screen large numbers of compounds rapidly and in parallel. For example, using microtiter plates and automated assay equipment, a laboratory can perform as many as 100,000 assays per day, or more, in parallel.

Tumor Model

The following description sets forth exemplary embodiments of the present technology. It should be recognized, however, that such description is not intended as a limitation on the scope of the present disclosure but is instead provided as a description of exemplary embodiments.

The present disclosure, in various embodiments, describes ex vivo primary tumor angiogenesis assays useful for assessing the capability of therapeutic agents in inhibiting tumor angiogenesis. The assays utilize an ex vivo primary tumor model generated from a fresh tumor block dissected from a primary tumor tissue. Under suitable conditions, endothelial cells grow out of the tumor block to surround the tumor block, providing a suitable model system for drug testing.

In the tumor model, or more specifically "tumor angiogenesis model" or "tumor endothelial cell or tissue model", the primary tumor cells are generally located within the tumor core while the newly grown endothelial cells are spread around and surrounding the tumor core. Such a spatial separation permits assessing a candidate anti-tumor agent's relative ability to kill endothelial cells versus tumor cells. Anti-tumor agents that kill both endothelial cells and tumor cells are more likely cytotoxic, while those that selectively kill tumor endothelial cells may be less toxic to normal cells, and thus may be much safer to patients.

The spatial separation of the tumor cells and the tumor endothelial cells in the tumor model can be visually examined under a microscope or with other suitable imaging technology. Endothelial cells growing out of the tumor core can form an outgrowth surrounding the tumor core in a 2-dimensional or 3-dimensional manner. Example structures of the tumor endothelial tissue model are illustrated in FIG. 1. Panel A presents a top view of the culture from the initial tumor embedding to the time of the start of the treatment when the tumor endothelial cells have grown out of the tumor. In this view, the newly grown endothelial cells exhibit a ring shape with the tumor core inside the ring.

In some scenarios, the tumor endothelial cells remain on the bottom of the dish during growth to form a layer of endothelial cells (side view, as illustrated in FIG. 1, panel B). The height (cross-sectional) of the endothelial cell outgrowth may be smaller than that of the tumor core.

In some scenarios, especially in human tumor endothelial tissue models, the growth of the endothelial cells may occur in 3-dimensions, e.g., such that the endothelial cells grow in all directions around the tumor core (see, e.g., side view in FIG. 1, panel C). Here, the peak height (cross-sectional) of the endothelial cell outgrowth may be the same as or even greater than that of the tumor core.

The spatial separation of the tumor endothelial cells from the tumor cells, therefore, is most pronounced in the top view (FIG. 1, panel A) or likewise in the bottom view. In this view, such as viewed from an inverted microscope, the tumor core has a radius, the entire tumor model has a greater radius, and their difference (marked as "diameter") represents the "width" of the endothelial cell outgrowth. In either scenario B or C, there is little overlap (top view) between the tumor cells and tumor endothelial cells. Accordingly, examination of each type of cells can be assessed independently of the assessment of the other type.

In some embodiments, the present disclosure provides a method for growing endothelial cells around a tumor tissue.

The method entails, in some embodiments, embedding a tumor tissue, e.g., having a diameter between 0.1 mm and 1.5 mm, in a biological matrix; and culturing the tumor tissue in the biological matrix under conditions to promote growth of endothelial cells from the tumor tissue, for a time sufficient to allow the tumor tissue to grow, e.g., to larger than 2 mm in diameter.

The tumor tissue, sometimes referred to as a tumor block, is preferably a primary tumor tissue dissected from a tumor sample obtained from a donor subject, such as an animal having a tumor, or a human cancer patient. The tumor tissue is preferably freshly extracted, e.g., has not been frozen since isolation from the donor subject, and/or has not been isolated from the donor for more than 0.5, 1, 1.5, 2, 2.5, 3, 3.5 or 4 hours prior to being cultured as described herein.

The tumor tissue can also be examined to ensure that it is suitable for culturing. The examination can be done microscopically, for instance. In some embodiments, the tumor tissue is preferably homogeneous, e.g., at least 50%, 60%, 70%, 80%, 85%, 90% or 95% of the cells in the tumor tissue are of the same cell type, or are cancerous. In some embodiments, the tumor tissue shows no substantial evidence of fibrosis, e.g., less than about 30%, 25%, 20%, 15%, 10%, 5% or 1% of the cells are fibrotic. In some embodiments, at least 50%, 60%, 70%, 80%, 85%, 90% or 95% of the cells in the tumor tissue are alive. In some embodiments, less than about 30%, 25%, 20%, 15%, 10%, 5% or 1% of the cells in the tumor tissue are necrotic. In some embodiments, no visible hemorrhage is detected in the tumor tissue.

The tumor tissue can be obtained from a mammalian subject, which can be human, or an experimental animal, such as a primate, a rat, a mouse, a rabbit, or a dog.

The tumor may be any solid tumor from the subject, such as a solid tumor from a bladder cancer, liver cancer, colon cancer, rectal cancer, endometrial cancer, pancreatic cancer, small cell lung cancer, non-small cell lung cancer, breast cancer, urethral cancer, head and neck cancer, gastrointestinal cancer, stomach cancer, esophageal cancer, ovarian cancer, renal cancer, melanoma, prostate cancer or thyroid cancer.

The size of the tumor tissue is an important factor for preparing the tumor model. The embedded tumor tissue, in some embodiments, has a diameter that is not greater than 1.5 mm. In some embodiments, the embedded tumor tissue has a diameter that is not greater than 1.4 mm, 1.3 mm, 1.2 mm, 1.1 mm, 1.0 mm, 0.9 mm, 0.8 mm, 0.7 mm, 0.6 mm, 0.5 mm, 0.45 mm, 0.4 mm, 0.35 mm, 0.3 mm, 0.25 mm, 0.2 mm, 0.15 mm or 0.1 mm. In some embodiments, the embedded tumor tissue has a diameter that is greater than 0.05 mm, 0.1 mm, 0.15 mm, 0.2 mm, 0.25 mm, 0.3 mm, 0.35 mm, 0.4 mm, 0.45 mm, 0.5 mm, 0.6 mm, 0.7 mm, 0.8 mm, 0.9 mm, 1.0 mm, 1.1 mm, or 1.2 mm. In some embodiments, the embedded tumor tissue has a diameter that is from 0.1 mm to 1.5 mm, 0.1 mm to 1.4 mm, 0.1 mm to 1.3 mm, 0.2 mm to 1.5 mm, 0.2 mm to 1.3 mm, 0.2 mm to 1.2 mm, 0.2 mm to 1.1 mm, 0.2 mm to 1.0 mm, 0.2 mm to 0.9 mm, 0.2 mm to 0.8 mm, 0.2 mm to 0.7 mm, from 0.2 mm to 0.6 mm, from 0.2 mm to 0.5 mm, from 0.2 mm to 0.4 mm, from 0.2 mm to 0.3 mm, from 0.3 mm to 0.7 mm, from 0.3 mm to 0.6 mm, from 0.3 mm to 0.5 mm, from 0.3 mm to 0.4 mm, from 0.4 mm to 0.7 mm, from 0.4 mm to 0.6 mm, from 0.4 mm to 0.5 mm, from 0.5 mm to 0.7 mm, from 0.5 mm to 0.6 mm, without limitation.

The use of the term "diameter" herein does not limit the shape of the tumor tissue to round. Rather, the diameter is an approximate measurement of the tissue so long as the tissue is not substantially flat or thin and elongated. For instance, the tumor tissue may have a dimension of 0.5 mm (H)×0.5 mm (L)×0.3 mm (D) with a total volume of 0.075 mm³. In another example, the tumor tissue has a dimension of 0.4 mm (H)×0.4 mm (L)×0.6 mm (D) with a total volume of 0.096 mm³.

The biological matrix used to embed the tumor tissue can be readily obtained from commercial sources, such as a simple type-1 collagen matrix or a Matrigel® gelatinous protein mixture. In some embodiments, the biological matrix is biologically compatible. In some embodiments, the biological matrix contains at least an angiogenic factor. In some embodiments, the biological matrix does not include an angiogenic factor; rather, the culture media (discussed below) includes an angiogenic factor. Non-limiting examples of angiogenic factors include VEGF, FGF (e.g., bFGF), EGF, and angiopoietin. A full-strength Matrigel, in some embodiments, is preferred, but a growth factor-reduced Matrigel can work as well. In some embodiments, the biological matrix includes at least VEGF. In some embodiments, the biological matrix includes at least bFGF. In some embodiments, the biological matrix includes at least EGF.

The biological matrix, in some embodiments, encloses (e.g., surrounds) the entire tumor tissue. The biological matrix, however, does not need to be particularly large. The embedding should allow growth factors or other nutrients in a culture medium to penetrate and reach the various surfaces of the tumor tissue while the tissue is being cultured. In some embodiments, the biological matrix has a thickness of at least 1 mm, or at least 2 mm, 3 mm, 4 mm, 5 mm, 6 mm, 7 mm, 8 mm, 9 mm, 10 mm, 15 or 20 mm outside the tumor tissue (e.g., between the tumor tissue and the walls of the container). In some embodiments, the biological matrix surrounding the tumor tissue (e.g., between the tumor tissue and the walls of the container) has a thickness that is less than 50 mm, 40 mm, 30 mm, 20 mm, 15 mm, 14 mm, 13 mm, 12 mm, 11 mm, 10 mm, 9 mm, 8 mm, 7 mm, 6 mm, or 5 mm.

The culture media for growing endothelial cells out of tumor tissue preferably contains an angiogenic factor such as VEGF, FGF (e.g., bFGF), EGF, and angiopoietin. Commercial growth media such as those available from Lonza (e.g., EGM-2 MW) and Promocell can be suitable for this purpose. In some embodiments, the culture medium includes at least VEGF. In some embodiments, the culture medium includes at least bFGF. In some embodiments, the culture medium includes at least EGF.

It is also noted that angiogenic factors, such as VEGF or bFGF, are not required to be included in the culture medium or the biological matrix. Even simple cell culture media that contain no supplemental growth factors can still cause the tumor endothelial cells to grow (e.g., DMEM plus 10% fetal bovine serum without any factors added).

The culturing time can be varied depending on the type of the tumor tissue, the biological matrix embedding the tumor tissue, the culture medium and the desired outcome. In some embodiments, the tumor tissue grows to at least 2 mm in diameter. In some embodiments, the tumor tissue grows to at least 2.5 mm, 3 mm, 3.5 mm, 4 mm, 4.5 mm, 5 mm, 5.5 mm, 6 mm, 6.5 mm, 7 mm, 7.5 mm, 8 mm, 8.5 mm, 9 mm, 9.5 mm or 10 mm in diameter. In some embodiments, the tumor tissue grows to a size that is not greater than 20 mm, 15 mm, 10 mm, 9 mm, 8 mm, 7 mm, 6 mm, 5 mm, 4 mm, or 3 mm in diameter before it is used for testing (e.g., drug testing). It is observed that, in general, it takes longer time to prepare a tissue model from a larger tumor tissue, but larger tumor tissues facilitate measurement of drug efficacy.

The tumor tissue can be embedded and cultured in a variety of cell culture plates, dishes, or other containers. In some embodiments, the container has a base having a diameter of at least 2 mm, or at least 2.5 mm, 3 mm, 3.5 mm, 4 mm, 4.5 mm, 5 mm, 5.5 mm, 6 mm, 6.5 mm, 7 mm, 7.5 mm, 8 mm, 8.5 mm, 9 mm, 9.5 mm, 10 mm, 20 mm, 50 mm or 100 mm. In some embodiments, the base has a diameter that is not greater than 100 mm, 50 mm, 30 mm, 20 mm, 15 mm, 10 mm, 9 mm, 8 mm, 7 mm, 6 mm, 5 mm, 4 mm, or 3 mm. In some embodiments, the base has a concave interior surface facing the tumor cells. In some embodiments, the base is substantially flat.

The cell culture container can take a multi-well format, in some embodiments. For instance, the cell culture container can have a 12-well, 24-well, 48-well, 96-well, 384-well format to facilitate higher throughput culturing, screening and comparison.

For a non-primate animal solid tumor tissue, it may take about 3 days, 4 days, 5 days or 6 days to grow into a desirable size. For a human tumor tissue, the culturing time needed may be at least a week, 10 days, 2 weeks, 18 days, 3 weeks or 4 weeks.

The present disclosure also provides, in some embodiments, a tumor model, or more specifically a tumor angiogenesis model or a tumor endothelial cell or tissue model. The provided tumor model can be capable of angiogenesis such that it is useful for testing a test agent's ability to inhibit tumor angiogenesis. More generally, the tumor model is able to allow a test agent to kill the endothelial cells within the tumor model or inhibit their growth, so as to reflect the agent's anti-angiogenesis activity. In addition, the test agent's impact on the tumor cells in the tumor core can also be assessed, e.g., at or about the same time as assessment of the agent's effect on the endothelial cells. An agent that preferentially kills tumor endothelial cells relative to tumor cells may be a preferred drug candidate. Selective killing of tumor endothelial cells can lead to tumor death by depriving it of nutrients and oxygen, e.g., without negatively affecting healthy cells and tissues to a significant extent. Non-specific killing of both tumor endothelial cells and tumor cells, by contrast, is more generally toxic to cells, which may include neighboring healthy cells, and thus may have more side effects than selective targeting of tumor endothelial cells. In some embodiments, the tumor model is prepared according to a method as disclosed herein.

The term "tumor model," "tumor angiogenesis model," or "tumor endothelial cell or tissue model," as used herein generally refers to a tumor tissue, preferably including new endothelial cells, grown from tumor cells obtained from a donor individual, wherein the tumor tissue can be used to assess a test agent's ability to kill endothelial cells in the tumor model. An ex vivo tumor model refers to a tumor model that includes at least one cell grown, ex vivo, from tumor cells isolated from the donor.

In some embodiments, the present disclosure provides a tumor model that is prepared ex vivo. In some embodiments, the tumor model includes an endothelial cell outgrowth surrounding a tumor core, wherein the tumor model has a diameter between 0.5 mm and 20 mm and the tumor core has a diameter that is greater than 0.2 mm but is not greater than 50% of the diameter of the tumor model.

The term "endothelial cell outgrowth" refers to a structure of cells in the tumor model which grew from the tumor core ex vivo. These newly grown cells may be less-densely disposed than the tumor cells in the tumor core which, by contrast, was isolated from a donor individual, such as a mouse xenograft tumor model or a human patient. In some embodiments, the cell density of the endothelial cell outgrowth is not greater than 50% (or not great than 20%, 30%, 40%, 60%, 70%, 80%, 90%, or 95%) of the cell density in the tumor core.

In some embodiments, a substantial portion (e.g., at least 30%, 40%, 50%, 60%, 70%, 80%, 90% or 95%) of the cells in the endothelial cell outgrowth are endothelial cells. Endothelial cells or endothelium are cells of the type that lines the interior surface of blood vessels and lymphatic vessels, forming an interface between circulating blood or lymph in the lumen and the rest of the vessel wall. Endothelial cells in direct contact with blood are called vascular endothelial cells.

Vascular endothelial cells line the entire circulatory system, from the heart to the smallest capillaries. These cells have unique functions in vascular biology. These functions include fluid filtration, such as in the glomerulus of the kidney, blood vessel tone, hemostasis, neutrophil recruitment, and hormone trafficking. Endothelium of the interior surfaces of the heart chambers is called endocardium.

In some embodiments, the endothelial cell outgrowth has a width (or "diameter" as illustrated in FIG. 1, panel A) which, for instance, can be measured as the difference between the radius of the tumor model and the radius of the tumor core inside the tumor model, of at least 1 mm, or at least 2 mm, 3 mm, 4 mm, 5 mm, 6 mm, 7 mm, 8 mm, 9 mm, 10 mm, 11 mm, 12 mm, 13 mm, 14 mm or 15 mm. In some embodiments, the endothelial cell outgrowth has a width of not greater than about 20 mm, 18 mm, 17 mm, 16 mm, 15 mm, 14 mm, 13 mm, 12 mm, 11 mm, 10 mm, 9 mm, 8 mm, 7 mm, 6 mm, or 5 mm.

In some embodiments, the width of the tumor endothelial cell outgrowth is greater than the radius of the tumor core. In some embodiments, the width of the tumor endothelial cell outgrowth is at least 1.5, 2, 2.5, or 3 times the radius of the tumor core.

In some embodiments, the tumor model has a diameter of at least 2 mm, or at least 3 mm, 4 mm, 5 mm, 6 mm, 7 mm, 8 mm, 9 mm, 10 mm, 11 mm, 12 mm, 13 mm, 14 mm, 15 mm, 20 mm, or 25 mm. In some embodiments, the tumor model has a diameter not greater than about 30 mm, 25 mm, 20 mm, 19 mm, 18 mm, 17 mm, 16 mm, 15 mm, 14 mm, 13 mm, 12 mm, 11 mm, 10 mm, 9 mm, 8 mm, 7 mm, 6 mm, or 5 mm.

In some embodiments, at least 50% of cells in the endothelial cell outgrowth are endothelial cells grown, ex vivo, from the tumor core. In some embodiments, at least 60%, 70%, 80%, 90% or 95% of the cells in the endothelial cell outgrowth are endothelial cells, e.g., grown, ex vivo, from the tumor core.

The tumor core, in some embodiments, has a diameter that is not greater than 2 mm, 1.5 mm, 1.2 mm, 1.1 mm, 1 mm, 0.9 mm, 0.8 mm or 0.7 mm. In some embodiments, the embedded tumor tissue has a diameter that is not greater than 0.6 mm, 0.5 mm, 0.45 mm, 0.4 mm, 0.35 mm, 0.3 mm, 0.25 mm, 0.2 mm, 0.15 mm or 0.1 mm. In some embodiments, the embedded tumor tissue has a diameter that is greater than 0.05 mm, 0.1 mm, 0.15 mm, 0.2 mm, 0.25 mm, 0.3 mm, 0.35 mm, 0.4 mm, 0.45 mm, or 0.5 mm. In some embodiments, the embedded tumor tissue has a diameter that is from 0.2 mm to 0.7 mm, from 0.2 mm to 0.6 mm, from 0.2 mm to 0.5 mm, from 0.2 mm to 0.4 mm, from 0.2 mm to 0.3 mm, from 0.3 mm to 0.7 mm, from 0.3 mm to 0.6 mm, from 0.3 mm to 0.5 mm, from 0.3 mm to 0.4 mm, from 0.4 mm to 0.7 mm, from 0.4 mm to 0.6 mm, from 0.4 mm to 0.5 mm, from 0.5 mm to 0.7 mm, from 0.5 mm to 0.6 mm, without limitation.

The tumor model preferably contains a sufficient number of live cells. In some embodiments, no more than 10% of the cells in the endothelial cell outgrowth are dead. In some embodiments, no more than 20%, 15%, 10%, 9%, 8%, 7%, 6%, 5%, 4%, 3%, 2% or 1% of the cells in the endothelial cell outgrowth are dead. In some embodiments, no more than 90%, 80%, 70%, 60%, 50%, 40%, 30%, 20% or 10% of the cells in the tumor core are dead.

In some embodiments, the tumor model contains at least a cell that is genetically modified. The genetic modification, in some embodiments, was made in the donor subject before the tumor tissue was isolated. In some embodiments, the genetic modification is made outside the donor subject but prior to culturing in the biological matrix. In some embodiments, the genetic modification is made when the tumor tissue is cultured in the biological matrix. In some embodiments, the genetic modification is made after new endothelial cells have grown in the tumor model. In some embodiments, the genetic modification is made after the tumor model has been cultured to a stage suitable for drug screening.

The genetic modification can be done with methods known in the art. In one example, the polynucleotide is introduced to a cell with a vector, such as a plasmid or a viral vector. Non-limiting examples of viral vectors include those prepared from viruses such as adeno-associated viruses and lentiviruses. In some embodiments, the genetic modification comprises editing of one or more sites in the genome of the cells. Such editing can be achieved, for instance, by a CRISPR/Cas (Clustered regularly interspaced short palindromic repeats/CRISPR-associated protein) system or associated base editors that integrate CRISPR/Cas with a APOBEC (apolipoprotein B mRNA editing enzyme, catalytic polypeptide-like) cytosine deaminase.

The genetic modification, in some embodiments, promotes the growth of endothelial cells. In some embodiments, the genetic modification can be found in certain tumor patients and therefore mimic the genetic profile in those patients. Non-limiting examples include mutations in KDR (e.g., T771R and A1065T) which may activate the expression of Vascular endothelial growth factor receptor 2 (VEGFR2) in vascular endothelial cells, and activating mutations in epidermal growth factor receptor (EGFR), e.g., L858R and delE746-A750.

In some embodiments, the genetic modification may inhibit the growth of the endothelial cells and thus introduction of the genetic modification prior to, during, or after establishment of the tumor model helps to evaluate the effect of the genetic modification as a potential treatment.

Screening Candidate Agents

Methods are also provided for testing the anti-tumor efficacy (e.g., capability of killing tumor cells, killing tumor endothelial cells, or inhibiting the growth of tumor or tumor endothelial cells) of a test agent. When an efficacious agent is in contact with the tumor model as disclosed here, the agent can kill some or all of the endothelial cells in the model, or at least reduce their rate of growth and/or proliferation. Thus, in certain embodiments, between prior to and after the contact, the numbers (or ratio) of live and dead cells in the tumor model (or in the endothelial cell outgrowth) will change. By the same token, by measuring such numbers or ratio, the efficacy of the agent can be determined.

In some embodiments, therefore, the method entails contacting a tumor model of the present disclosure with the candidate agent ex vivo; and determining the ratio of live to dead cells in the endothelial cells of the tumor model, wherein a decrease of ratio as compared to prior to the admixing indicates that the candidate agent is capable of killing the tumor endothelial cells. Further, the ratio of live to dead cells in the tumor core can also be measured, prior to and following the treatment. Preferred agents would selectively kill tumor endothelial cells, relative to tumor cells in the tumor core, indicated as a larger decrease of the ratio of live to dead tumor endothelial cells and a smaller, or no, decrease of the ratio of live to dead tumor cells in the tumor core.

Determination of the live and dead status of the cells can be carried out with suitable dyes, for instance. A dye that shows live cells can be fluorescein diacetate (FDA). A dye that shows the cells being dead can be propidium iodide (PI), without limitation. Counting of live and dead cells can be done under inverted microscope, or any other suitable analytical methods known in the art.

The viability determination of the cells in the model can be done with other methods as well. For instance, trypan blue is an azo dye that selectively colors dead cells as it is not able to pass through the intact cell membranes of live cells. Another example dye is 7-Aminoactinomycin D (7-AAD) which can stain compromised cell membranes. In another example, the viability of a cell can be assessed by bioluminescent detection of the ATP level via luciferase catalyzed reactions in the cell. In some embodiments, definitive counts of live and dead cells are not required. A relative change of viability of the cells in the model can be sufficient for purpose of evaluating an agent for its impact on such viability. Morphological changes can also indicate the impact of the test agent on endothelial cells.

Figures 2A, 2B, 2C, 2D:
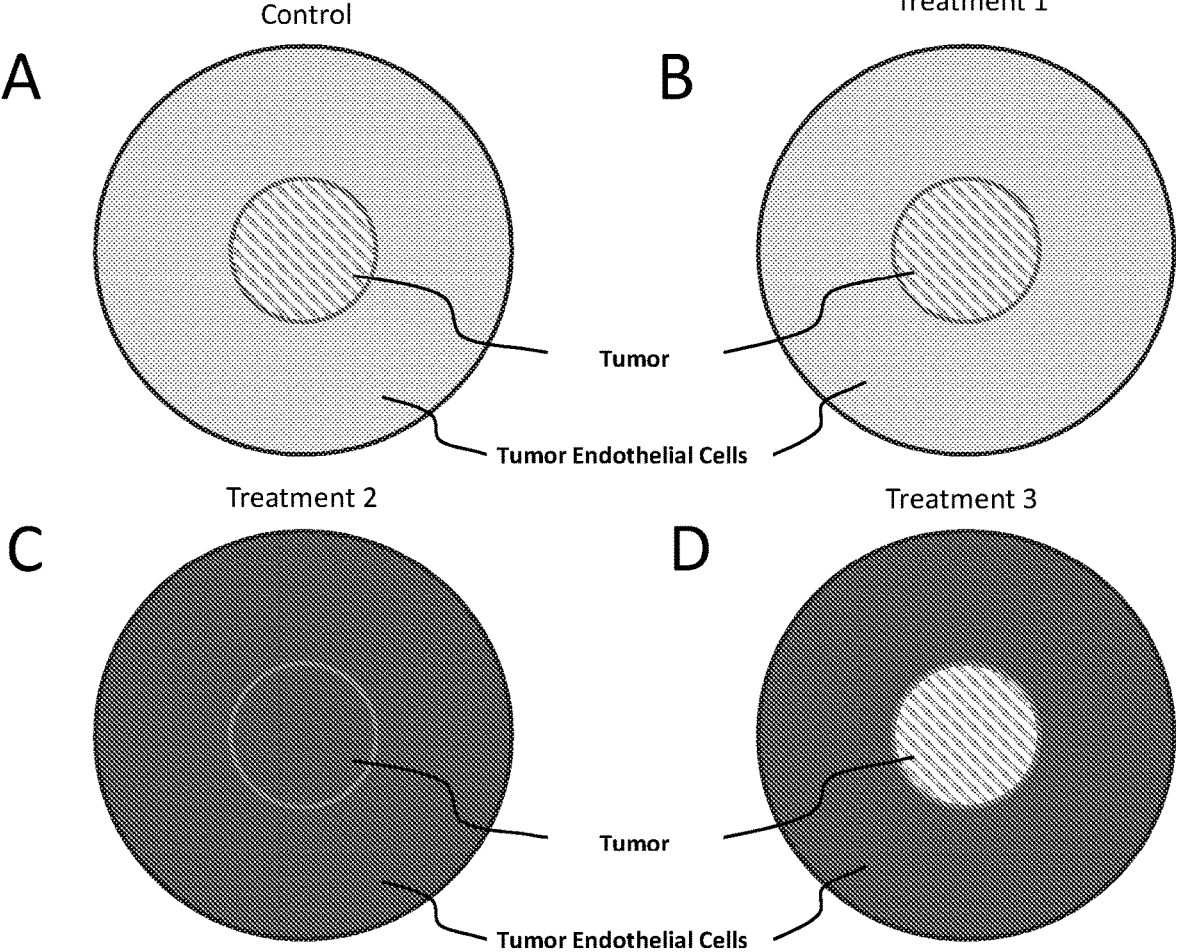
FIGS. 2A-2D illustrate an exemplary method of assessing cell death specificity in a tumor endothelial cell model. live cells are indicated by the light gray, dead cells are indicated by dark gray; and mixtures of live cells and dead cells are indicated by shading with diagonal stripes.

Such methods are demonstrated in the accompanying experimental examples and are further illustrated in FIG. 2. In the figure (top view of the tumor model), live cells are indicated by the light gray, dead cells are indicated by dark gray; and mixtures of live cells and dead cells are indicated by shading with diagonal stripes. In the control without treatment, the tumor endothelial cells are alive (light gray) while the tumor core is a mixture (shading) due to the inefficient diffusion of nutrient or oxygen into the tumor that causes a certain amount of cell death (Panel A). An agent that has no effect on tumor endothelial cell death would be similar to the control treatment (Panel B). An agent that indiscriminately kills all cells and has nonspecific toxicity would kill both the tumor and tumor endothelial cells (Panel C). An agent that kills tumor endothelial cells without significantly affecting the tumor core is a highly specific agent for tumor endothelial cells (Panel D).

A few particular advantages of the tumor models disclosed herein can be readily appreciated. First, the instant inventors have determined that assessing endothelial cell death is more advantageous than assessing endothelial cell growth because the ability to kill endothelial cells is much less influenced by the intrinsic variability in growth rate than the ability to inhibit endothelial cell growth. In addition, an agent that can kill tumor blood vessels would be more potent therapeutically than an agent that only inhibits growth. Second, these new models can distinguish agents that specifically kill tumor endothelial cells from agents that have nonspecific cellular toxicity.

Provided herein are also kits and packages that include two or more ingredients and/or agents useful for practicing any method of the present disclosure. In one example, the kit or package includes a biological matrix, a culture medium, and preferably suitable containers and/or dissecting tools. In another example, the kit or package includes dyes for selectively staining live and/or dead cells.

EXAMPLES

The following examples are included to demonstrate specific embodiments of the disclosure. It should be appreciated by those of skill in the art that the techniques disclosed in the examples which follow represent techniques to function well in the practice of the disclosure, and thus can be considered to constitute specific modes for its practice. However, those of skill in the art should, in light of the present disclosure, appreciate that many changes can be made in the specific embodiments which are disclosed and still obtain a like or similar result without departing from the spirit and scope of the disclosure.

Example 1: Establishment of an Ex Vivo Primary Tumor Angiogenesis Model

This example describes a procedure to prepare a primary tumor angiogenesis model for assessing the efficacy of anti-cancer candidate agents.

Protocol:

1. The day before the experiment, all necessary tools were sprayed with 70% ethanol and sterilized under UV light overnight, including blade, dissecting and micro-dissecting scissors and biceps. 24-well dishes were placed at 4° C. to pre-chill plates and Matrigel was thawed, 24 hours before tumor dissection.

2. 70% ethanol was sprayed on working bench. Two sterile petri dishes were prepared with 10 ml sterile PBS. The following steps 3 and 4 are necessary for mouse tumor models. For fresh human tumor, steps 3 and 4 are skipped.

3. The tumor-bearing mice were euthanized. 70% ethanol was sprayed on the mouse and the tumor was removed using sterilized dissecting tools (avoid the fur). The tumor was rinsed in petri dish with sterile PBS to remove ethanol and fur. The tumor was transferred to a new petri dish with PBS for dissection. The dish is placed on ice.

4. Pre-chilled sterile pipet tips were used to seed regular Matrigel in 24 well plates on ice. Matrigel (30 μl) was dropped in the middle of each well without touching the edge of the well (avoid introducing bubbles if possible).

5. The tumor was cut in halves using the sterile blade. Healthy tumor tissue that is not necrotic and is within the tumor capsule was identified and isolated. The healthy tumor tissue was cut into small pieces. For instance, a suitable size for the tumor tissue is 0.5 mm (H)×0.5 mm (L)×0.3 mm (D) with a total volume of 0.075 mm³.

6. Each tumor piece was gently transferred and embedded in the Matrigel drop in the 24-well plate. The embedded piece was placed in the bottom and middle of each Matrigel drop. The plate was kept on ice all the time.

7. After seeding the tumor pieces, plates were incubated in a 37° C. cell culture incubator without medium for 10 minutes in order for the Matrigel to solidify.

8. Endothelial Growth Medium (0.5 ml) was added to each well and incubated at 37° C. with 5% $CO_2$. Treatment was not added until the new endothelial cells was grown out of the tumor or were larger than 3 mm in diameter. This usually takes 4 days for the LL2 Lewis lung cancer model and 7 days for the CT26 colon cancer model. For human tumor models, the growth time is typically 2-3 weeks, depending on the tumor type. Media was changed every 4 days during prolonged culture. Typically, when the tumor tissue grows to 2 mm in diameter, it was good for drug testing. A size of about 3 mm in diameter can make visualization easier.

9. When the assay was ready to be analyzed for cell death (e.g., 48 hours after drug addition), the dye mixture was prepared by mixing 6 μl of green dye to stain live cells (5 mg/ml Fluorescein diacetate or FDA in DMSO) with 30 μl of red dye (2.5 mg/ml Propidium iodide or PI in PBS) to stain dead cells in an Eppendorf tube. The FDA dye needs to be stored frozen in a −20° C. freezer because it has a labile ester bond.

10. 1 μl of the dye mixture was added to each well of the 24-well dish. It is usually preferred to do one 24-well dish at a time given the amount of time needed to take pictures (the green dye is not as stable in the cells in the long term).

11. The dish was gently rocked a few times to mix the dye with the media in the wells and incubate the dish at 37° C. for 10 min (too long incubation can make the green signal too intense).

12. Each well was washed with 0.5 ml of sterile PBS and then 0.5 ml of phenol red free SFM was added to each well. Alternatively 0.5 ml of regular Endothelial Cell Growth Media can be added to each well if this well needs to be continuously maintained after the experiment.

13. An inverted microscope using the 2× objective lens was used to observe morphological changes in the experimental wells.

14. Taking pictures in the red and green channels would allow not only the recording of the results but also more accurate quantitation of the results. To take pictures for all the wells, first a well that has robust red and green signals was picked. A picture at the red channel using the optimal setting (remember this setting) was taken and then a picture at the green channel using another optimal setting (remember this setting) was taken. The final picture is the merged picture of the red and green channels. Pictures of all other wells were taken in each channel using the same settings so that different wells can be compared.

Example 2: Mouse Colon Cancer Model

Figures 3A, 3B, 3C, 3D:
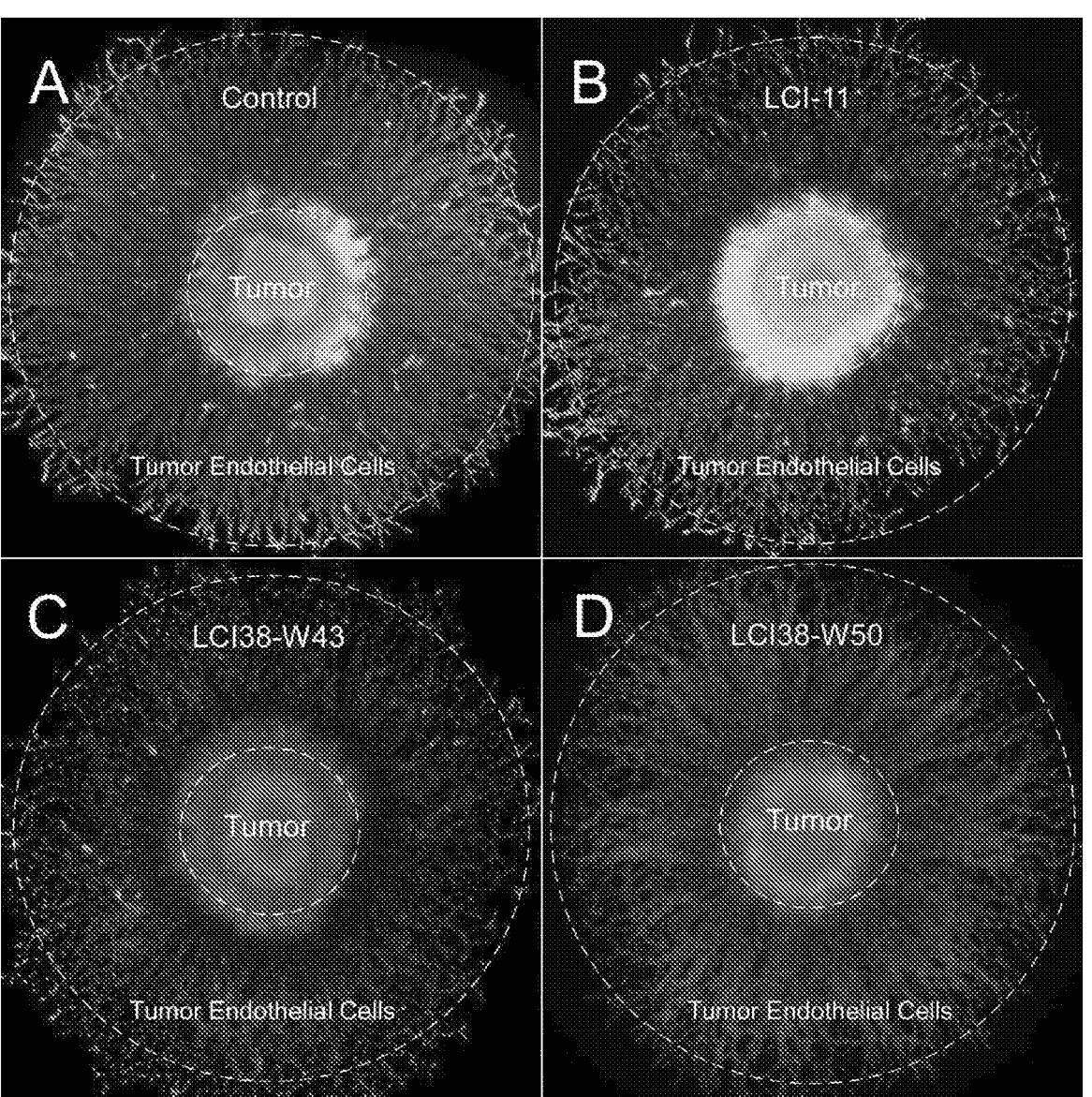
FIGS. 3A-3D present images showing the establishment and testing of a tumor endothelial cell 3D model using a mouse colon cancer tumor.

Drug Testing:

A tumor from xenograft mouse model of colon cancer (CT26.CL25) was grown using the method described herein to establish an ex vivo model of tumor angiogenesis. Treatment did not start until the new tumor endothelial cells had grown for 7 days. After drug treatment was done for two days, cell survival was assessed by a two-color assay using a mixture of fluorescein diacetate (green dye) and propidium iodide (red dye). Green cells represented live cells. Red cells represented dead cells. Orange cells represented a mixture of live and dead cells. As shown in FIG. 3, the inner white circle delineates the location of the tumor and the outer white circle delineates the outer growth of tumor endothelial cells. FIG. 3A. Control vehicle treated; FIG. 3 B. 20 μM LCI-11 treated; FIG. 3C. 20 μM LCI38-W43 treated; and FIG. 3D. 20 μM LCI38-W50 treated. Each of LCI-11, LCI38-W43 and LCI38-W50 were test antitumor drugs.

In the control experiment (FIG. 3A), all tumor endothelial cells (cells grown out of the tumor between the two circles)

and most of the tumor were alive (green). However, part of the middle of the tumor contained dead cells (orange) likely due to the inefficient diffusion of nutrient or oxygen into the inner tumor. In the LCI-11-treated sample (FIG. 3B), some tumor endothelial cells were killed (red) while the tumor was similar to the control. In the LCI38-W43-treated sample (FIG. 3C), most of the tumor endothelial cells were killed (red) while the tumor was similar to the control. Even the remaining live tumor endothelial cells (green) had changed their morphology from the elongated shape to small dots. The preferential killing of tumor endothelial cells indicated the specificity of this compound towards tumor endothelial cells. In the LCI38-W50-treated sample (FIG. 3D), all tumor endothelial cells and all tumor cells were killed (red). The indiscriminate killing of tumor endothelial cells and tumor cells demonstrates the lack of specificity of this compound. This technique can therefore exclude nonspecific reagents that are generally cytotoxic and do not specifically kill tumor endothelial cells as antiangiogenic agents. This is also a unique advantage of this technology.

Example 3: Mouse Lung Cancer Model

Figures 4A, 4B, 4C, 4D:
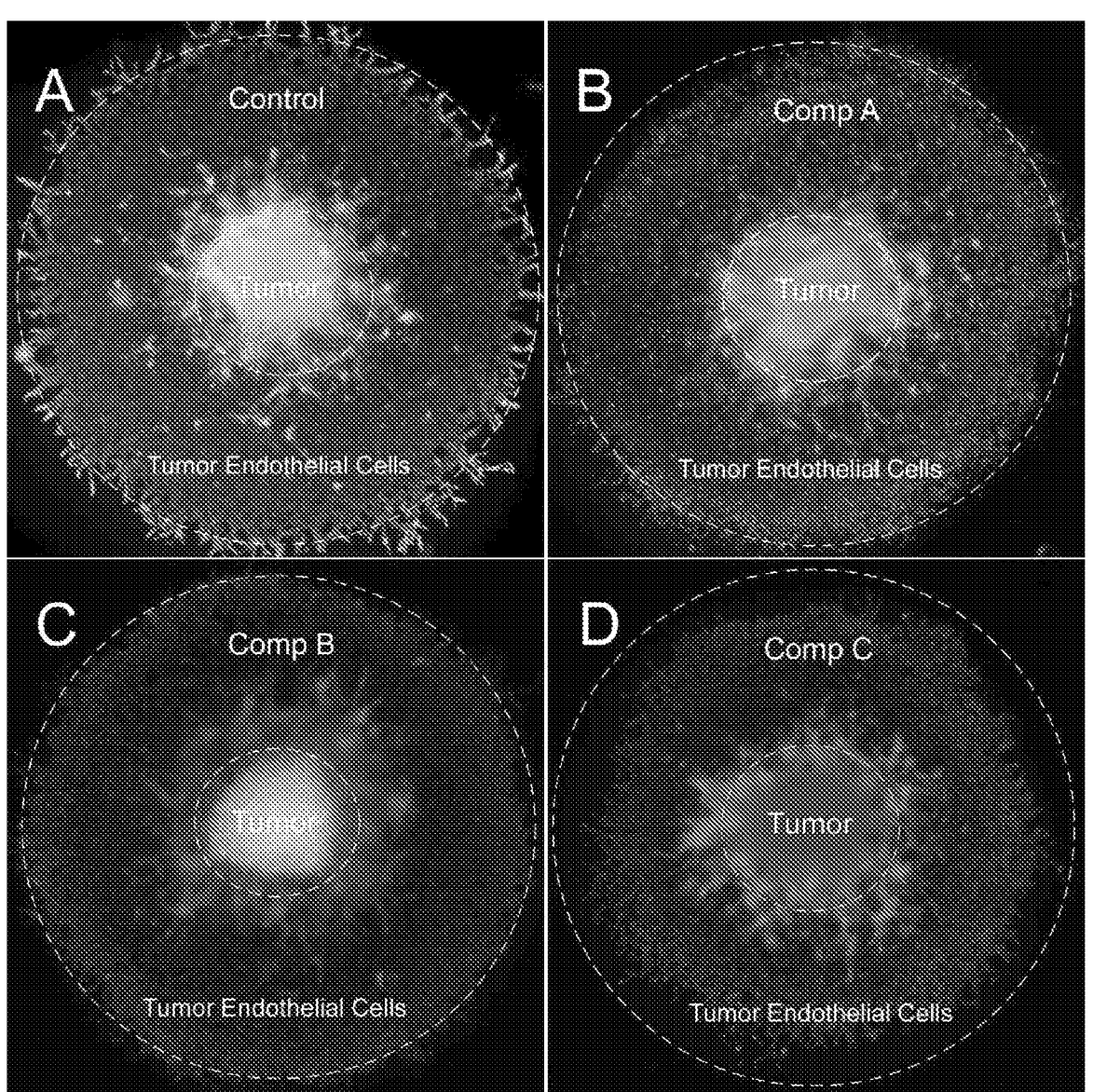
FIGS. 4A-4D present images showing the establishment and testing of a tumor endothelial cell 3D model using a mouse lung cancer tumor.

A tumor from xenograft mouse model of lung cancer (LL/2) was grown using the methods described herein to establish an ex vivo model of tumor angiogenesis. Treatment did not start until the new tumor endothelial cells had grown for 5 days. After drug treatment was done for two days, cell survival was assessed by a two-color assay using a mixture of fluorescein diacetate (green dye) and propidium iodide (red dye). Green cells represented live cells. Red cells represented dead cells. Orange cells represented a mixture of live and dead cells. The inner white circle delineated the location of the tumor and the outer white circle delineates the outer growth of tumor endothelial cells (FIG. 4). FIG. 4A Control vehicle-treated; FIG. 4B. 20 μM Comp A-treated; FIG. 4C. 20 μM Comp B-treated; and FIG. 4D. 20 μM Comp C-treated. Each of the compounds, Comp A, Comp B, and Comp C, was a candidate antitumor drug.

In the control experiment (FIG. 4A), all tumor endothelial cells (cells grown out of the tumor between the two circles) and most of the tumor were alive (green). However, part of the middle of the tumor contained dead cells (orange) likely due to the inefficient diffusion of nutrient or oxygen into the inner tumor. In the Comp A-treated sample (FIG. 4B), some tumor endothelial cells were killed (red) while the tumor is similar to the control. The killed endothelial cells were the newest endothelial cells because they were located in the outer rim of the tumor endothelial cell growth. In the Comp B-treated sample (FIG. 4C), all tumor endothelial cells are killed (red) while the tumor was still alive (green). The preferential killing of tumor endothelial cells indicated the specificity of this compound towards tumor endothelial cells. In the Comp C-treated sample (FIG. 4D), all tumor endothelial cells and all tumor cells were killed (red). The indiscriminate killing of tumor endothelial cells and tumor cells shows the lack of specificity of this compound. This technique can therefore exclude nonspecific reagents that are generally cytotoxic and do not specifically kill tumor endothelial cells as antiangiogenic agents.

Unless otherwise defined, all technical and scientific terms used herein have the same meaning as commonly understood by one of ordinary skill in the art to which this invention belongs.

The inventions illustratively described herein may suitably be practiced in the absence of any element or elements, limitation or limitations, not specifically disclosed herein. Thus, for example, the terms "comprising", "including," "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed.

Thus, it should be understood that although the present invention has been specifically disclosed by preferred embodiments and optional features, modification, improvement and variation of the inventions embodied therein herein disclosed may be resorted to by those skilled in the art, and that such modifications, improvements and variations are considered to be within the scope of this invention. The materials, methods, and examples provided here are representative of preferred embodiments, are exemplary, and are not intended as limitations on the scope of the invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

In addition, where features or aspects of the invention are described in terms of Markush groups, those skilled in the art will recognize that the invention is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

It is to be understood that while the disclosure has been described in conjunction with the above embodiments, that the foregoing description and examples are intended to illustrate and not limit the scope of the disclosure. Other aspects, advantages and modifications within the scope of the disclosure will be apparent to those skilled in the art to which the disclosure pertains.

The invention claimed is:

1. A method for growing endothelial cells around a tumor tissue, comprising:
    embedding a tumor tissue in a biological matrix, wherein the tumor tissue has a diameter between 0.1 mm and 1.5 mm, is substantially homogeneous, and is substantially free of fibrosis, necrosis or hemorrhage, and wherein the biological matrix comprises at least an angiogenic factor selected from VEGF, FGF, EGF and angiopoietin; and
    culturing the tumor tissue in the biological matrix under conditions to promote growth of endothelial cells from the tumor tissue, for a time sufficient such that the tumor tissue grows into a tumor model comprising at least one endothelial cell outgrowth surrounding a tumor core, and wherein the tumor model has a diameter of at least 3 mm.

2. The method of claim 1, wherein the tumor tissue has a dimension of 0.5 mm×0.5 mm×0.3 mm.

3. The method of claim 1, wherein the tumor tissue has a volume of 0.010 mm$^3$ to 0.099 mm$^3$.

4. The method of claim 3, wherein the tumor tissue has a volume of 0.075 mm$^3$.

5. The method of claim 1, wherein the tumor tissue is allowed to grow to larger than 2 mm in diameter.

6. The method of claim 1, wherein the tumor tissue is allowed to grow to larger than 3 mm in diameter.

7. The method of claim 1, wherein the tumor tissue is allowed to grow to larger than 4 mm in diameter.

8. The method of claim 1, wherein the tumor tissue is allowed to grow to larger than 8 mm in diameter.

9. The method of claim 1, wherein the tumor tissue, prior to the embedding, has not been frozen since isolation from the donor subject.

10. The method of claim 1, wherein no more than 10% of the cells in the tumor tissue are necrotic.

11. The method of claim 1, wherein the embedded tumor tissue is prepared by dissection from a larger tumor block isolated from a donor subject.

12. The method of claim 11, wherein the tumor block has been isolated from the donor subject less than 12 hours before the embedding.

13. The method of claim 1, wherein the biological matrix comprises a gelatinous protein mixture.

14. The method of claim 13, wherein the gelatinous protein mixture is not growth factor-reduced.

* * * * *